(12) United States Patent
Kim et al.

(10) Patent No.: US 11,007,519 B2
(45) Date of Patent: May 18, 2021

(54) CHIP STRUCTURE FOR MULTIPLE MOLECULAR DIAGNOSES

(71) Applicant: GMD BIOTECH, INC., Gwangju (KR)

(72) Inventors: Min Gon Kim, Gwangju (KR); Hyou Arm Joung, Gwangju (KR); Youngung Seok, Gwangju (KR)

(73) Assignee: GMD BIOTECH, INC., Gwangju (KR)

( * ) Notice: Subject to any disclaimer, the term of this patent is extended or adjusted under 35 U.S.C. 154(b) by 44 days.

(21) Appl. No.: 16/067,394

(22) PCT Filed: Dec. 9, 2016

(86) PCT No.: PCT/KR2016/014420
§ 371 (c)(1),
(2) Date: Jun. 29, 2018

(87) PCT Pub. No.: WO2017/116037
PCT Pub. Date: Jul. 6, 2017

(65) Prior Publication Data
US 2019/0022639 A1    Jan. 24, 2019

(30) Foreign Application Priority Data
Dec. 29, 2015  (KR) .......................... 10-2015-0188179

(51) Int. Cl.
*B01L 3/00*       (2006.01)
*B01L 7/00*       (2006.01)
*C12Q 1/68*       (2018.01)
*C12Q 1/6844*     (2018.01)

(52) U.S. Cl.
CPC .......... *B01L 3/5027* (2013.01); *B01L 3/5023* (2013.01); *C12Q 1/6844* (2013.01); *B01L 7/52* (2013.01); *B01L 2300/0887* (2013.01); *B01L 2300/126* (2013.01); *C12Q 2563/107* (2013.01)

(58) Field of Classification Search
CPC ............ C12Q 1/6844; C12Q 2563/107; B01L 3/5027; B01L 3/5023; B01L 7/52; B01L 2300/0887
See application file for complete search history.

(56) References Cited

U.S. PATENT DOCUMENTS

2005/0196779 A1* 9/2005 Ho .................... B01L 3/502738
                                                              435/6.11
2013/0004665 A1* 1/2013 Lehtinen ............... G03F 7/0002
                                                              427/210

FOREIGN PATENT DOCUMENTS

| CN | 203688494 U | 7/2014 |
| JP | 2000-236876 A | 9/2000 |
| JP | 2008-245612 A | 10/2008 |
| KR | 10-1080087 B1 | 11/2011 |
| KR | 10-2012-0099486 A | 9/2012 |
| KR | 10-1257975 B1 | 4/2013 |

OTHER PUBLICATIONS

International Search Report for PCT/KR2016/014420 dated Mar. 13, 2017, citing the above reference(s).
Chinese Office Action dated Dec. 13, 2019 corresponding to Chinese Application No. 201680077723.9, citing the Above reference.

* cited by examiner

*Primary Examiner* — David C Thomas
(74) *Attorney, Agent, or Firm* — Hauptman Ham, LLP

(57) ABSTRACT

A multiple molecular diagnosis chip structure according to one embodiment of the present invention comprises: a reaction pad; a channel pad; and a transfer pad.

9 Claims, 8 Drawing Sheets
Specification includes a Sequence Listing.

Non

Target 1

Target 1,2

Target 1,2,3

SEQUENCE LISTING

<160> NUMBER OF SEQ ID NOS: 18

<210> SEQ ID NO 1
<211> LENGTH: 18
<212> TYPE: DNA
<213> ORGANISM: Artificial
<220> FEATURE:
<223> OTHER INFORMATION: primer F3 targeting S.agalactiae

<400> SEQUENCE: 1
ggaactctag tggctggt                                                          18

<210> SEQ ID NO 2
<211> LENGTH: 20
<212> TYPE: DNA
<213> ORGANISM: Artificial
<220> FEATURE:
<223> OTHER INFORMATION: primer B3 targeting S.agalactiae

<400> SEQUENCE: 2
caatcacatc tgttaaggct                                                        20

<210> SEQ ID NO 3
<211> LENGTH: 42
<212> TYPE: DNA
<213> ORGANISM: Artificial
<220> FEATURE:
<223> OTHER INFORMATION: primer FIP targeting S.agalactiae

<400> SEQUENCE: 3
gccatttgct gggcttgatt gctgtattag aagtacatgc tg                               42

<210> SEQ ID NO 4
<211> LENGTH: 42
<212> TYPE: DNA
<213> ORGANISM: Artificial
<220> FEATURE:
<223> OTHER INFORMATION: primer BIP targeting S.agalactiae

<400> SEQUENCE: 4
tgaggctatt actagcgtgg aatctacacg actaccaata ga                               42

<210> SEQ ID NO 5

```
<211> LENGTH: 21
<212> TYPE: DNA
<213> ORGANISM: Artificial
<220> FEATURE:
<223> OTHER INFORMATION: primer LF targeting S.agalactiae

<400> SEQUENCE: 5
acttgtggag ttgtcacttg a                                              21

<210> SEQ ID NO 6
<211> LENGTH: 18
<212> TYPE: DNA
<213> ORGANISM: Artificial
<220> FEATURE:
<223> OTHER INFORMATION: primer LB targeting S.agalactiae

<400> SEQUENCE: 6
agacttcatt gcgtgcca                                                  18

<210> SEQ ID NO 7
<211> LENGTH: 20
<212> TYPE: DNA
<213> ORGANISM: Artificial
<220> FEATURE:
<223> OTHER INFORMATION: primer F3 targeting S.pneumoniae

<400> SEQUENCE: 7
aactgattga aagccattca                                                20

<210> SEQ ID NO 8
<211> LENGTH: 18
<212> TYPE: DNA
<213> ORGANISM: Artificial
<220> FEATURE:
<223> OTHER INFORMATION: primer B3 targeting S.pneumoniae

<400> SEQUENCE: 8
gtcaacgtgg tctgagtg                                                  18

<210> SEQ ID NO 9
<211> LENGTH: 43
<212> TYPE: DNA
<213> ORGANISM: Artificial
<220> FEATURE:
<223> OTHER INFORMATION: primer FIP targeting S.pneumoniae

<400> SEQUENCE: 9
cctgcttcat ctgctagatt gcaaagaaga gttcatgacg gac                      43

<210> SEQ ID NO 10
<211> LENGTH: 40
<212> TYPE: DNA
<213> ORGANISM: Artificial
<220> FEATURE:
<223> OTHER INFORMATION: primer BIP targeting S.pneumoniae

<400> SEQUENCE: 10
tgccgaaaac gcttgataca tgtttggttg gttattcgtg                          40

<210> SEQ ID NO 11
<211> LENGTH: 24
<212> TYPE: DNA
<213> ORGANISM: Artificial
<220> FEATURE:
<223> OTHER INFORMATION: primer LF targeting S.pneumoniae

<400> SEQUENCE: 11
```

-continued gtaagagttc gatataaagg cggt                                            24

<210> SEQ ID NO 12
<211> LENGTH: 25
<212> TYPE: DNA
<213> ORGANISM: Artificial
<220> FEATURE:
<223> OTHER INFORMATION: primer LB targeting S.pneumoniae

<400> SEQUENCE: 12
ggagtttagc tggaattaaa acgca                                           25

<210> SEQ ID NO 13
<211> LENGTH: 23
<212> TYPE: DNA
<213> ORGANISM: Artificial
<220> FEATURE:
<223> OTHER INFORMATION: primer F3 targeting S.aureus

<400> SEQUENCE: 13
agaagtgatt ctgaagatcc aac                                             23

<210> SEQ ID NO 14
<211> LENGTH: 23
<212> TYPE: DNA
<213> ORGANISM: Artificial
<220> FEATURE:
<223> OTHER INFORMATION: primer B3 targeting S.aureus

<400> SEQUENCE: 14
tatcagttct ttgacctttg tca                                             23

<210> SEQ ID NO 15
<211> LENGTH: 43
<212> TYPE: DNA
<213> ORGANISM: Artificial
<220> FEATURE:
<223> OTHER INFORMATION: primer FIP targeting S.aureus

<400> SEQUENCE: 15
taaccgtatc accatcaatc gagtatacag tgcaacttca act                       43

<210> SEQ ID NO 16
<211> LENGTH: 45
<212> TYPE: DNA
<213> ORGANISM: Artificial
<220> FEATURE:
<223> OTHER INFORMATION: primer BIP targeting S.aureus

<400> SEQUENCE: 16
gtcaaacaat gacattcaga ctggaccata tttctctaca cctttt                    45

<210> SEQ ID NO 17
<211> LENGTH: 22
<212> TYPE: DNA
<213> ORGANISM: Artificial
<220> FEATURE:
<223> OTHER INFORMATION: primer LF targeting S.aureus

<400> SEQUENCE: 17
ttaattaatg tcgcaggttc tt                                              22

<210> SEQ ID NO 18
<211> LENGTH: 22
<212> TYPE: DNA

```
<213> ORGANISM: Artificial
<220> FEATURE:
<223> OTHER INFORMATION: primer LB targeting S.aureus

<400> SEQUENCE: 18
gatacacctg aaacaaagca tc                                                  22
```

CHIP STRUCTURE FOR MULTIPLE MOLECULAR DIAGNOSES

CROSS REFERENCE TO RELATED APPLICATION

This present application is a national stage filing under 35 U.S.C § 371 of PCT application number PCT/KR2016/014420 filed on Dec. 9, 2016 which is based upon and claims the benefit of priority to Korean Patent Application No. 10-2015-0188179 filed on Dec. 29, 2015 in the Korean Intellectual Property Office. The disclosures of the above-listed applications are hereby incorporated by reference herein in their entirety.

TECHNICAL FIELD

The present invention relates to a chip structure for multiple molecular diagnosis, and more particularly, to a chip structure for multiple molecular diagnosis capable of performing all the processes of molecular diagnosis by only one sample injection.

BACKGROUND ART

Molecular diagnosis or Molecular diagnosis refers to a diagnostic field or technique of detecting or analyzing biomarker materials (especially DNA or RNA) using molecular biological techniques, and, particularly, is used in a similar meaning to nucleic acid diagnosis. Since the development of the polymerase chain reaction in particular, in 1985, and technological advances have been made, such as a completion of a genetic map of various infectious organisms including humans, molecular diagnosis technique is rapidly developed.

Currently, the mainly used method for virus detection is molecular diagnosis method, which detects nucleic acid (nucleic acid: DNA and RNA or their variants) of bacteria and viruses, etc. that is a cause of diseases, and detects the cause and the infection or not of the disease. The molecular diagnosis method consists of four steps: a sample collection from a body fluid, a gene extraction of the collected sample, and an amplification and analysis using a polymerase chain reaction. Since the molecular diagnosis method can undergo a gene amplification course, accurate diagnosis with very high sensitivity and specificity for even a minimum quantity pathogen is possible. However, in order to perform the existing diagnostic methods, high-cost analysis equipment and the reagents and high-cost analysis equipment such as PCR and electrophoresis, etc., is used, and thus, they are costly, and it requires complex and specialized techniques, and thus, they can be performed only by skilled engineers. In addition, due to the enormous size of analysis equipment, an integration of each bioreactor step is difficult and the possibility of sample contamination is always contained in the molecular diagnosis process. Since it takes long time to analysis, there are limitations to the gene diagnosis in the field.

Therefore, a new pathogen gene analysis system with high efficiency and high sensitivity has been needed to overcome the disadvantages of existing gene diagnosis techniques and to enable gene diagnosis in the field. As an alternative, lab-on-a-chip (LOC) technique is spotlighted. Lab-on-a-chip technique is a typical example of NT, IT, and BT convergence technologies, and refers to technique that all preprocessing and analysis steps of the sample such as sample dilution, mixing, reaction, separation, and quantification are performed on one chip using technologies such as MEMS and NEMS. Because of the features capable of automating and rapidly performing all reactions on a palm-sized chip, studies have been made for many years to miniaturize sample preprocessing, PCR, and analysis systems, and studies with regard to the gene analysis system integrated with the above it have been progressed significantly.

In gene analysis, amplification of DNA through PCR is essential for nucleic acid analysis since it amplifies the gene from a minimum quantity sample and has high sensitivity and specificity. Thermal cycling PCR method is a series of reactions that precisely match three temperature steps of a denaturation and a junction extension, and thus, expensive equipment is required for accurate temperature gradient. An isothermal PCR was developed to overcome it. Unlike the thermal cycling method, the isothermal PCR method can denature and junction extend at a constant temperature so that an amplification time can be shortened. It has an advantage which can perform it even in low price equipment capable of the isothermal maintenance. Therefore, it is advantageous to miniaturize equipment and can be applied regardless of the places such as a laboratory or a detection site.

Recently, a lot of studies have been produced to embody isothermal PCR on a microchip by using a lab-on-a-chip (LOC) or micro overall analysis system technique. This isothermal PCR method may refer to a method which enables the molecular diagnosis in the field test (POC test). Field diagnosis sensors using the isothermal PCR have been developed, but there are various problems such as a miniaturization, a cost reduction, a simple structure realization. Since the diagnosis sensor used in the field diagnosis test should be simpler and portable, a diagnosis sensor of being more miniaturized and capable of simple molecular diagnosis is needed.

The matters described as the above-mentioned background art is merely for the purpose of promoting an understanding of the background of the present invention and is not to be construed as an admission that it corresponds to the related art already known to those skilled in the art.

DISCLOSURE

Technical Problem

The present invention has been made in order to solve such a problem, and it is an object of the present invention to provide a paper chip structure for multiple molecular diagnosis which can be diagnosed immediately by using isothermal PCR method in the field with a simpler configuration.

Technical Solution

In order to accomplish the above object, a multiple molecular diagnosis chip structure according to one embodiment of the present invention includes: a reaction pad having a sample passage hole formed therethrough and a plurality of reaction patterns formed thereon, wherein an injected sample to be diagnosed can pass through the sample passage hole, and a reaction solution that includes an isothermal amplification primer for a specific nucleic acid to be diagnosed, an amplification enzyme, and an indicator having fluorescence varying depending on amplification exists in the reaction patterns; a channel pad disposed on the lower surface of the reaction pad, the channel pad having a first sample passage channel formed in a position corresponding to the sample passage hole, and a second sample passage channel corresponding to the reaction patterns; and a transfer pad disposed on the lower surface of the channel pad to transfer a sample, which is injected from the sample passage hole and transferred through the first sample passage channel, to the reaction patterns through the second sample passage channel.

The reaction solution may further include PVA.

It can further include a cover which is disposed on the upper surface of the reaction pan and having a sample injection part formed in a position corresponding to the sample through hole.

The reaction pattern includes at least two of the comparison patterns for confirming whether a sample is input and the detection patterns for detecting a specific DNA contained in the sample to be diagnosed.

An isothermal amplification primer and an amplification enzyme for specific DNA, respectively can exist in the detection pattern.

An upper case formed at an upper portion of the reaction pad and having a sample input part corresponding to the sample passage hole and the upper case having the patter confirmation part formed in a position corresponding to the reaction pattern, and a lower case which is formed at a lower portion of the transfer pad and is coupled with the upper case can be further included.

The reaction pad may be a porous glass membrane.

The channel pad may be a nitrocellulose or a polyether sulfone membrane.

The transfer pad may be a membrane having an asymmetric structure in which a pore size is reduced in a downward direction.

The indicator may include HNB (Hydroxynaphthol Blue).

Advantageous Effects

According to a paper chip structure for multiple molecular diagnoses according to the present invention, molecular diagnosis can be performed with a simpler configuration, so that molecular diagnosis can be performed more easily in the field. All the processes of molecular diagnosis can be performed by only one sample injection, and a portability is strengthened, and it is possible to proceed various molecular diagnosis simultaneously with one sample.

BEST MODE

The terminology used herein is for the purpose of mentioning the particular embodiments only and is not intended to limit the invention. The singular forms used herein include the plural forms unless the phrases do not express the opposite meaning explicitly. The meaning of "comprising" used in the specification embodies a particular feature, a region, an integer, a step, an operation, an element and/or a component, and does not exclude the existences or the additions of other specific feature, a region, an integer, a step, an operation, an element, a component, and/or a group.

Unless otherwise defined, all terms including the technical and scientific terms used herein have the same meaning as that of being generally understood by those skilled in the art to which this invention pertains. The terms which are generally used and defined previously are further constructed to have a meaning coincident with the related technical literature and the matter disclosed presently, and are not to be construed as ideal or very formal meanings unless otherwise defined.

Hereinafter, the multiple molecular diagnosis chip structure will be described by the preferred embodiment of the present invention with reference to the accompanying drawings.

Figure 1:
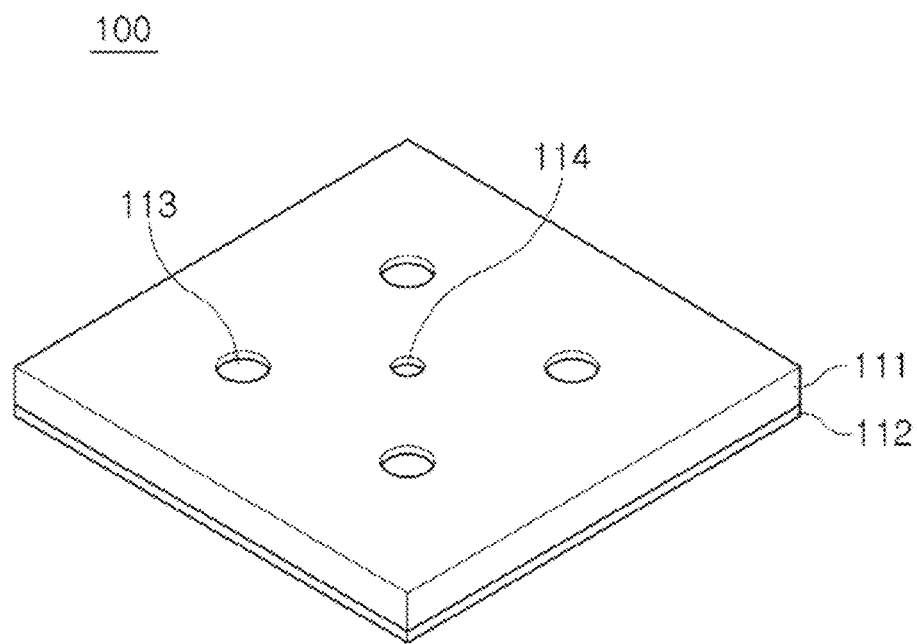
FIG. 1 is a perspective view illustrating a chip structure for a multiple molecular diagnosis in accordance with an exemplary embodiment of the present invention.
Figure 2:
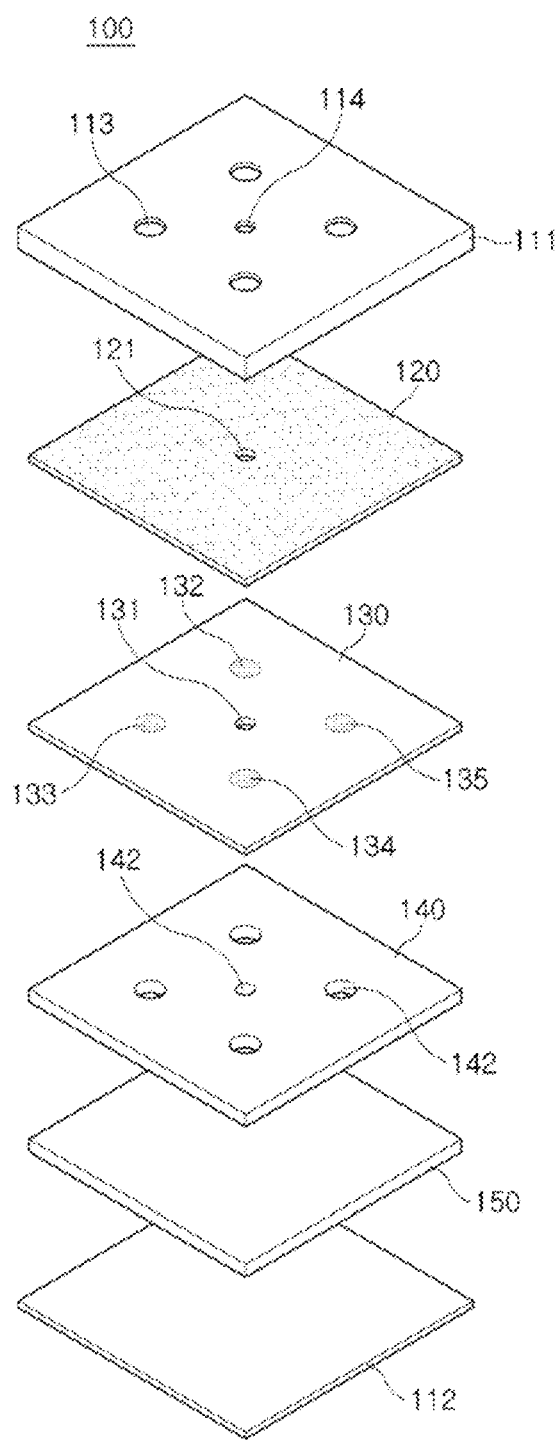
FIG. 2 is an exploded perspective view illustrating a chip structure for multiple molecular diagnosis in accordance with an exemplary embodiment of the present invention.
Figure 3A:
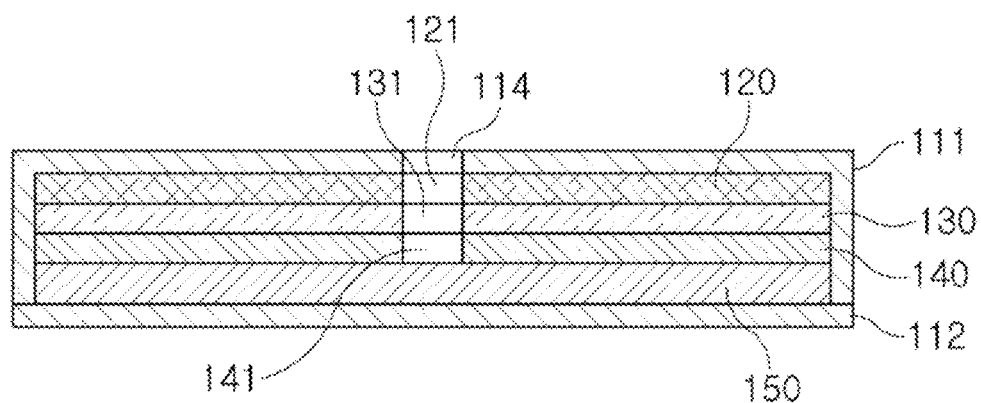
FIG. 3a is a cross-sectional view illustrating a chip structure for multi-molecular diagnosis in accordance with an exemplary embodiment of the present invention.
Figure 3B:
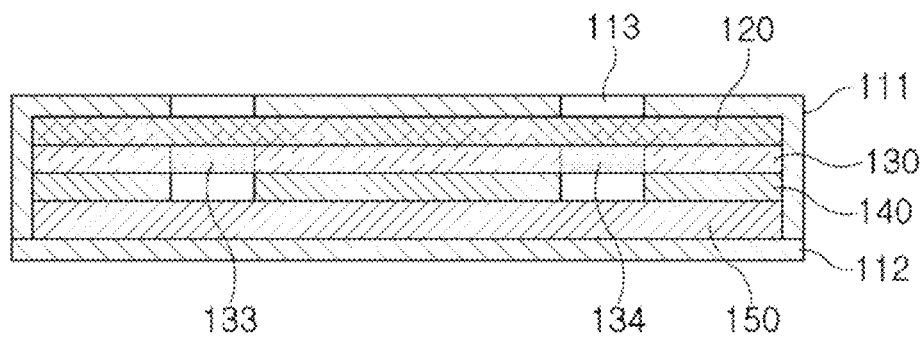
FIG. 3b is a cross-sectional view illustrating a chip structure for multi-molecular diagnosis in accordance with an exemplary embodiment of the present invention.

The present invention relates to a molecular diagnosis chip structure used in diagnosis equipment capable of detecting pathogens, viruses, and the like through an isothermal amplification method (LAMP) of nucleic acids such as DNA or RNA included in a sample to be diagnosed. FIG. 1 is a perspective view illustrating a chip structure for multiple molecular diagnosis in accordance with an exemplary embodiment of the present invention. FIG. 2 is an exploded perspective view illustrating a chip structure for multiple molecular diagnosis in accordance with an exemplar embodiment of the present invention. FIG. 3 is a cross-sectional view illustrating a chip structure for a multiple molecular diagnosis in accordance with an exemplary embodiment of the present invention. In a description with regard to the present invention with reference to FIGS. 1 to 3, the multiple molecular chip structure 100 in accordance with an exemplary embodiment of the present invention may largely include an upper case 111, a lower case 112, a cover 120, a reaction pad 130, a channel pad 140, and a transfer pad 150.

A core structure of the present invention is a structure in which the reaction pad 130, the channel pad 140, and the transfer pad 150 are laminated. The reaction pad 130 is subjected to an isothermal amplification of the sample to be diagnosed. The channel pad 140 separates and transfers the sample to be diagnosed, which causes the isothermal amplification, to the reaction pad 130, and the transfer pad 150 serves to convey the sample to be diagnosed to the reaction pad stably.

Hereinafter, each configuration will be described in more detail.

In the present invention, the upper case 111 and the lower case 112 maintain the shape of a chip having a laminated structure of the cover 120, the reaction pad 130, the channel pad 140, and the transfer pad 150, and serve to protect them from the outside. Since the cover 120 and each pad 130, 140, and 150 uses a membrane material, the upper case 111 and the lower case 112 are required to maintain the shape. Such the upper case 111 and the lower case 112 are to maintain the structure of the chip, and can perform a diagnosis function of the chip even if they are omitted. The upper case 111 can be formed with a sample input part 114 through which a sample can be input, at its center. Also, a pattern confirmation part 113 capable of confirming the result of the isothermal amplification in the reaction pad 130 may be formed. The pattern confirmation part 113 may have an opening shape in which the reaction patterns 132, 133, 134, and 135 of the reaction pad 130 may be exposed, and a transparent window may be formed such that the change of the inside color can be confirmed. The sample input part 114 may be formed at a position corresponding to the sample input part 131 of the cover 120 laminated on the lower portion thereof. Various materials can be used for the upper case 111 and the lower case 112, but a light plastic material is preferable.

A cover 120 may be formed on the lower portion of the upper case 111. The cover 120 is installed to prevent the reaction solution present in the reaction patterns 132, 133, 134, and 135 of the reaction pad 130 and the diagnosis sample to be input from being evaporated. Further, it is preferable to use it as a transparent material so as to confirm the amplification or not in the reaction patterns 132, 133, 134, and 135. A sample input part 121 is formed in the center of the cover 120, at a position corresponding to the sample input part 114 of the upper case 111 and the sample passage hole 131 of the reaction pad 130. In this embodiment, an ELISA tape sold for the experiments can be used by cutting to an appropriate size.

It is preferable that the reaction pad 130 uses a membrane having a plurality of pores formed, capable of the isothermal amplification and capable of showing a fluorescence of a fluorescent dye. For an example, a glass membrane made of a glass material can be used. The reaction pad 130 has a sample passage hole 131 formed therethrough and a plurality of reaction patterns 132, 133, 134, 135 formed thereon, wherein an injected sample to be diagnosed can pass through the sample passage hole at its center, and a reaction solution that includes an isothermal amplification primer for a specific nucleic acid to be diagnosed, and an indicator having fluorescence varying depending on amplification exists in the reaction patterns. In the present embodiment, a total of four reaction patterns are formed. The comparison pattern 132 may include only an indicator so as to confirm whether the sample has arrived or not. In the first detection pattern 133, the second detection pattern 134, and the third detection pattern 135, the reaction solution may exist, which includes an isothermal amplification primer for each separate nucleic acid, an amplification enzyme, and an indicator having fluorescence varying depending on amplification. Further, the unreacted additives may be further included for stabilization of the amplification enzyme and the indicator. As such unreactive additives, PVA is preferable.

Therefore, when four reaction patterns are present as in the embodiment of the present invention, three molecular diagnoses can be simultaneously performed through the amplification of three specific nucleic acids. It is possible to control the number of the reaction patterns and simultaneously control the kinds to be diagnosed.

Figure 4:
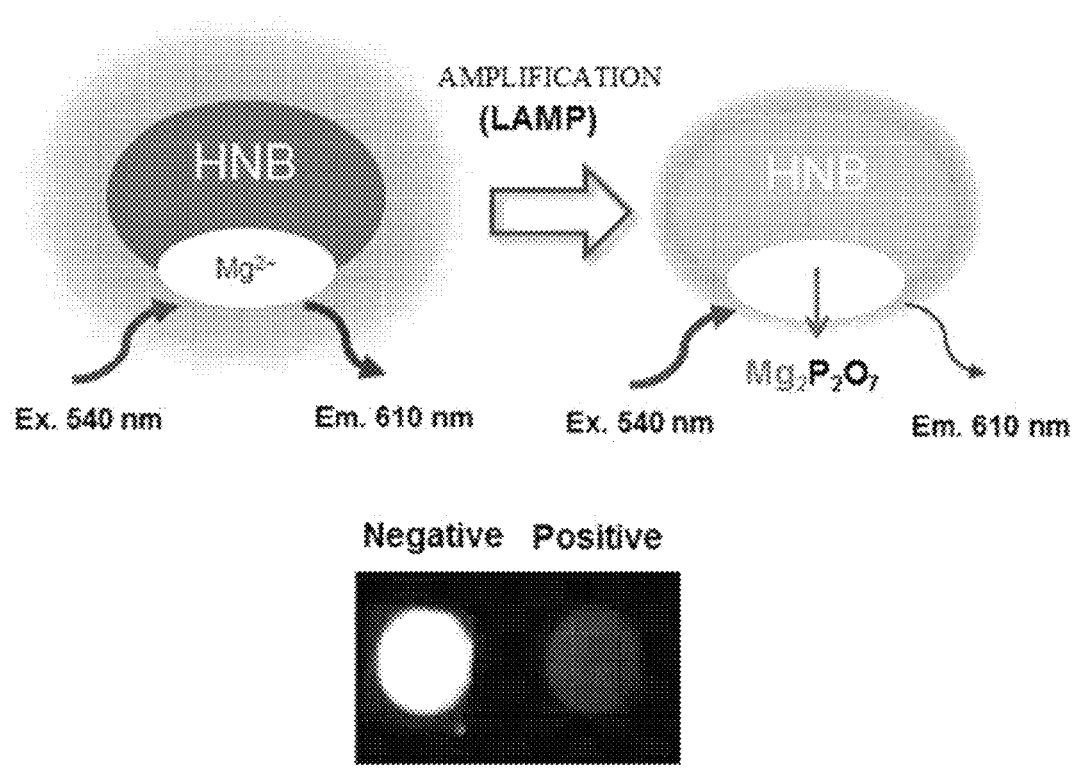
FIG. 4 is a picture illustrating a reaction of HNB (Hydroxynaphthol Blue) used in the present invention.

The indicator used in the reaction solution may be HNB (Hydroxynaphthol Blue). FIG. 4 is a picture showing the reaction of HNB used in the present invention. As shown in FIG. 4, HNB is an indicator that fluorescence is reduced when there is an amplification. Therefore, when the sample to be diagnosed is present, an amplification occurs, and fluorescence of HNB is decreased, so that the presence of the sample to be diagnosed can be known.

A channel pad 140 is formed in a lower portion of the reaction pad 130. The channel pad 140 serves to convey the sample to the reaction patterns 132, 133, 134, and 135 of the reaction pad 130 through the transfer pad 150. The first sample passage channel 141 is formed such that the sample passes in a position corresponding to the sample input part 114 of the upper case 111, the sample input part 121 of the cover, and the sample passage hole 131 of the reaction pad 130, and the second passage channel 142 is formed such that the sample passes from the transfer pad 150 in a position corresponding to the reaction patterns 132, 133, 134, and 135 of the reaction pad 130. It is preferable to use a membrane which the pannan is easy and does not impede the reaction such that it is easy to from each sample passage channel, with patterning the wax. In the present embodiment, a nitrocellulose or a polyether sulfone membrane can be used.

The transfer pad 150 is installed in the lower portion of the channel pad 140 to uniformly spread the injected sample to be diagnosed and supply the sample to the reaction patterns 132, 133, 134 and 135 of the reaction pad 130. As the transfer pad 150, an asymmetric membrane can be used, which has a reduced pore size in the downward direction so that the input sample can be well spread entirely. The sample to be input may spread to the smaller pore, and spread over the transfer pad 150 entirely and evenly.

Figure 5A:
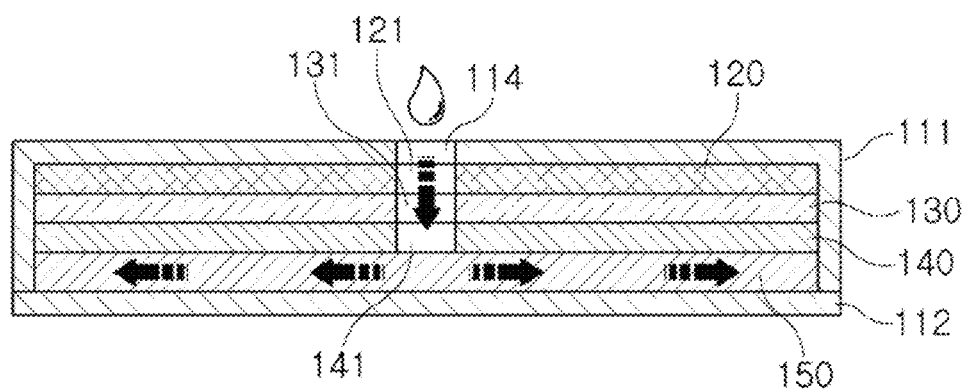
FIG. 5a is a view illustrating a sample movement of a chip structure for multiple molecular diagnosis in accordance with an exemplary embodiment of the present invention.
Figure 5B:
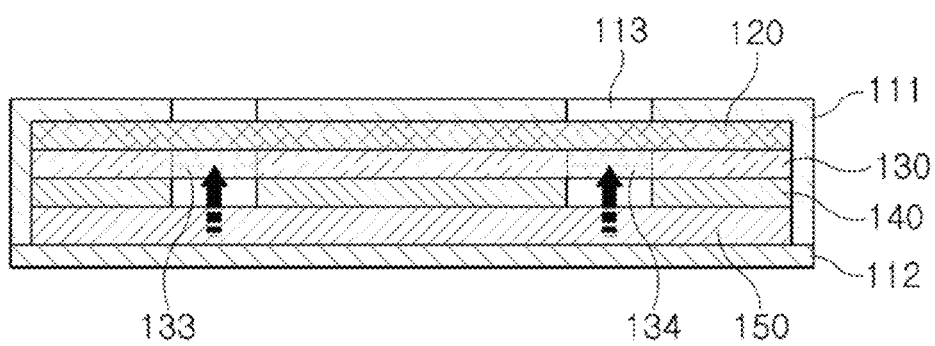
FIG. 5b is a view illustrating a sample movement of a chip structure for multiple molecular diagnosis in accordance with an exemplary embodiment of the present invention.

FIG. 5 is a view illustrating a sample movement of a chip structure for multiple molecular diagnosis in accordance with an exemplary embodiment of the present invention. When the sample is input through the sample input part 114 of the initial upper case 111, it moves to the transfer pad 150 through the sample input part 121 of the cover 120, the sample passage hole 131 of the reaction pad 130, and the first sample passage channel 141 of the channel pad 140. At this time, when the transfer pad 150 is sufficiently wetted, through the transfer pad 150, the sample reaches the reaction pattern 132, 133, 134, and 135 of the reaction pad 130 through the second sample passage channel 142 of the channel pad 140. By allowing the sample to reach the reaction patterns 132, 133, 134, and 135 independently through the channel pad 140, it is possible to perform multiple diagnosis by one sample injection.

Hereinafter, the experimental examples will be described in more detail.

1. Preparation of Multiple Molecular Diagnosis Chip

Multiple molecular diagnosis chips were prepared in the same manner as in FIGS. 1 to 3. First, a reaction pad was prepared using a G028 glass conjugated pad of Merck Millipore. A hole was formed in the middle and a reaction pattern was formed in four places. LAMP primers of targets 1, 2, and 3, respectively, which are desired to be diagnosed, were prepared. Target 1 was chosen as *Streptococcus agalactiae*, Target 2 as *Streptococcus pneumonia*, and Target 3 as *Staphylococcus aureus*. For example, the examples of DNA primers corresponding to targets 1, 2, and 3 are shown in Table 1 below. Primers corresponding to *Streptococcus pneumonia* were mixed with F3/B3/FIP/BIP/LF/LB in the order of 1:1:8:8:4:4.

TABLE 1

| target | primer | SEQ ID NOs | sequences |
|---|---|---|---|
| S. agalactiae (target 1) | F3 | 1 | GGAACTCTAGTGGCTGGT |
|  | B3 | 2 | CAATCACATCTGTTAAGGCT |
|  | FIP | 3 | GCCATTTGCTGGGCTTGATTGCTGT ATTAGAAGTACATGCTG |
|  | BIP | 4 | TGAGGCTATTACTAGCGTGGAATCT ACACGACTACCAATAGA |
|  | LF | 5 | ACTTGTGGAGTTGTCACTTGA |
|  | LB | 6 | AGACTTCATTGCGTGCCA |
| S. pneumoniae (target 2) | F3 | 7 | AACTGATTGAAAGCCATTCA |
|  | B3 | 8 | GTCAACGTGGTCTGAGTG |
|  | FIP | 9 | CCTGCTTCATCTGCTAGATTGCAAA GAAGAGTTCATGACGGAC |
|  | BIP | 10 | TGCCGAAAACGCTTGATACATGTTT GGTTGGTTATTCGTG |
|  | LF | 11 | GTAAGAGTTCGATATAAAGGCGGT |
|  | LB | 12 | GGAGTTTAGCTGGAATTAAAACGCA |
| S. aureus (target 3) | F3 | 13 | AGAAGTGATTCTGAAGATCCAAC |
|  | B3 | 14 | TATCAGTTCTTTGACCTTTGTCA |
|  | FIP | 15 | TAACCGTATCACCATCAATCGAGTA TACAGTGCAACTTCAACT |

TABLE 1-continued

| target | primer | SEQ ID NOs | sequences |
|---|---|---|---|
|  | BIP | 16 | GTCAAACAATGACATTCAGACTGGA CCATATTTCTCTACACCTTT |
|  | LF | 17 | TTAATTAATGTCGCAGGTTCTT |
|  | LB | 18 | GATACACCTGAAACAAAGCATC |

As such, LAMP primers necessary for each target were prepared, and the reaction solutions shown in Table 2 below were prepared.

TABLE 2

|  | PVA (10 kDa) | Primer | Polymerase | HNB | Water |
|---|---|---|---|---|---|
| Final concentration | 3% (w/v) | 4 uM | 0.32 U/uL | 240 uM | — |
| Stock concentration | 20% | 100 uM | 8 U/uL | 1.2 mM | — |
| Volume | 7.5 uL | 2.6 uL | 2 uL | 10 uL | 27.9 uL |
| Remark | Sigma | Mixture of F3, B3, FIP, BIP, LF and LB | Wako Chemical | Sigma | Using Total 50 uL of DNA-free water |

About 3.5 µl of the reaction solution was input into the reaction pattern of the reaction pad as shown in Table 2, and then dried in an oven at about 37° C. for about 20 minutes.

The channel pad was prepared by forming a pattern such that the sample passage channel can be formed on the surface through a wax printer, by using Sterlitech PES802005 8.0 µm membrane filter. SealPlate of Excel Scientific was overlaid with a reaction pad by a cover and a channel pad to form a sample input part, a sample passage hole and a first sample passage channel, respectively.

Multiple molecular diagnosis chip was prepared by laminating it using Vivid GF asymmetric membrane with the transfer panel, and subsequently, laminating the upper case and the lower case.

2. Performing of Multiple Molecular Diagnosis Reaction

A sample containing the DNA of targets 1, 2, and 3 groups to be diagnosed was prepared. It was mixed with the buffer solution and sample shown in Table 3 below.

TABLE 3

|  | Tris-HCl | KCl | MgSO$_4$ | (NH$_4$)$_2$SO$_4$ | Tween 20 | Betaine | dNTPs |
|---|---|---|---|---|---|---|---|
| Final concentration | 20 mM | 10 mM | 8 mM | 10 mM | 0.1% | 0.8M | 2.8 mM each |
| Stock concentration | 1.5M | 1M | 100 mM | 1M | 100% | 5M | 100 mM each |

After mixing the sample and the buffer solution, about 70 to 100 μl was injected through the sample injection part of the upper case, and the case was maintained at about 63° C. for about 1 hour, and the molecular diagnosis result was confirmed. (Non is the case where only the buffer solution is input, Target 1 is the case where only Target 1 sample is input, Targets 1 and 2 are the case where only Targets 1 and 2 samples are input, and Targets 1, 2 and 3 are the case where targets 1, 2 and 3 are input. See FIG. 6)

Figure 6:
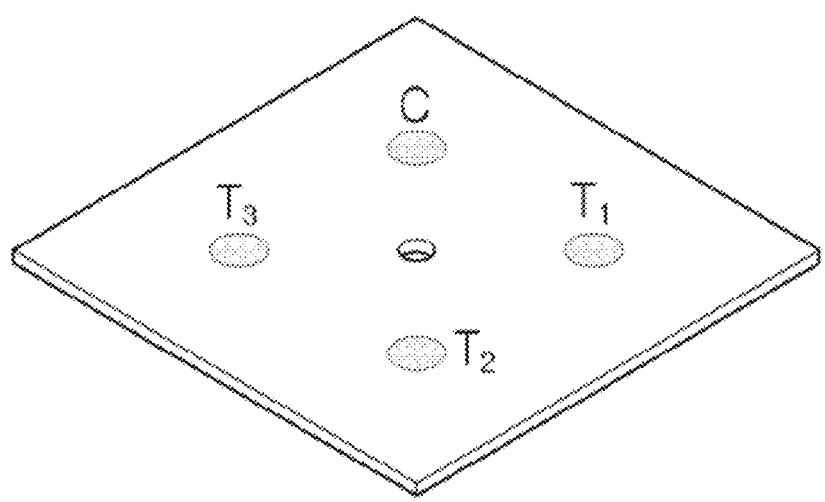
FIG. 6 is a view illustrating an experimental result using a chip structure for self-weight molecular diagnosis in accordance with an exemplary embodiment of the present invention.
Figure 7:
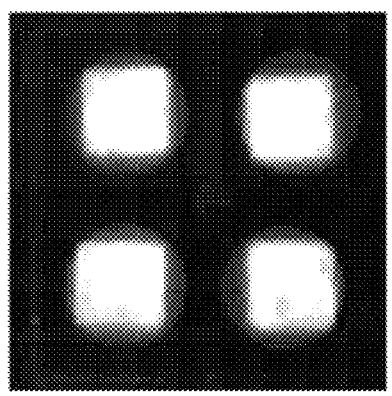
FIG. 7 is a picture illustrating an experimental result using a chip structure for self-weight molecular diagnosis in accordance with an exemplary embodiment of the present invention.
Figure 7:
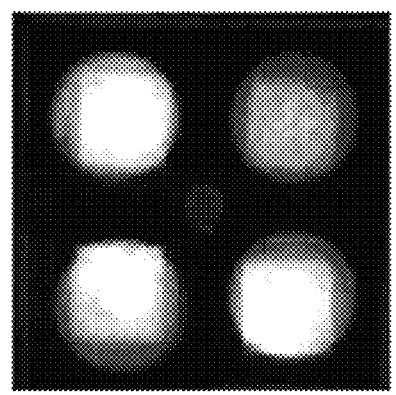
Figure 7:
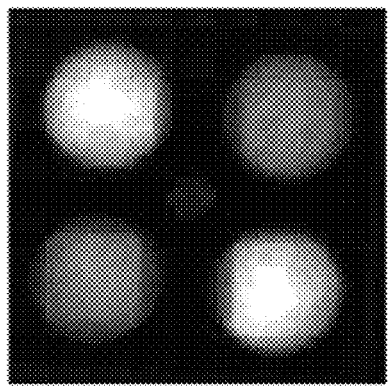
Figure 7:
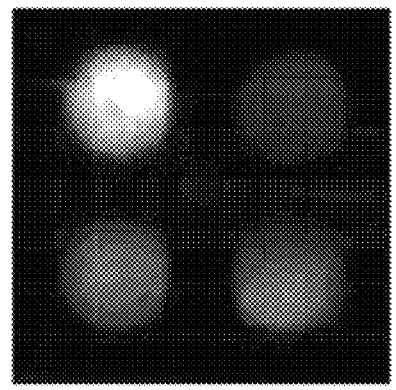
Figure 8:
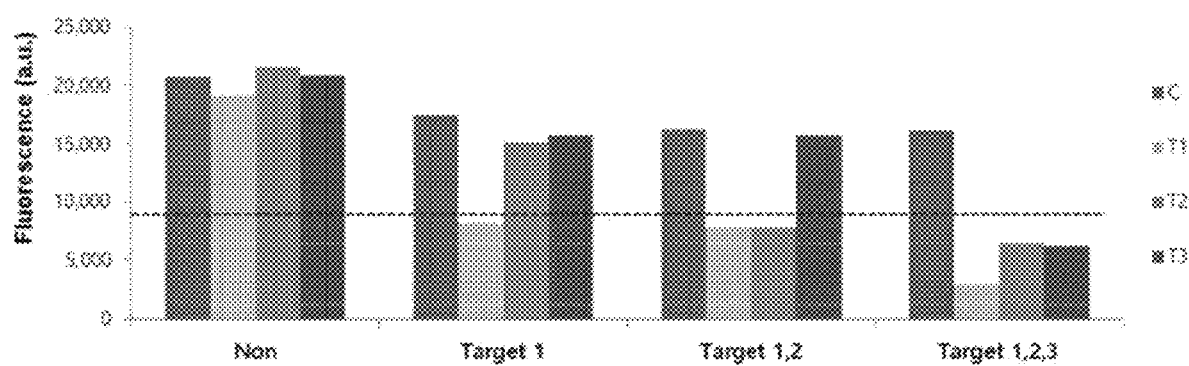
FIG. 8 is a graph showing an experimental result using a chip structure for self-weight molecular diagnosis in accordance with an exemplary embodiment of the present invention.

FIG. 7 is a picture illustrating the experimental results using a chip structure for self-weight molecular diagnosis in accordance with an exemplary embodiment of the present invention. FIG. 8 is a graph illustrating the experimental results using a chip structure for self-weight molecular diagnosis in accordance with an exemplary embodiment of the present invention. As shown in FIGS. 6 and 7, when there is no sample (Non), the isothermal amplification reaction is not performed, and it can be confirmed that the fluorescent substance exists, in all each region. In case of Target 1, it can be seen that there is a sample of Target 1 and fluorescence of T1 is decreased. In case of Target 2, it can be seen that there are the samples of Targets 1 and 2, and fluorescence of T1 and T2 decreases. In case of Target 3, it can be seen that there are the samples of Targets 1, 2, and 3, and fluorescence of T1, T2, and T3 decreases.

Thus, it can be seen that three molecular diagnoses can be performed simultaneously through a simple apparatus through the present invention.

While the embodiments of the present invention have been described with reference to the accompanying drawings, it will be understood by those skilled in the art to which the present invention pertains that the present invention may be performed in other specific forms without changing the technical idea or the essential characteristics.

Therefore, it is to be understood that the above-described embodiments are illustrative in all aspects and not restrictive. The scope of the present invention is represented by the claims described later rather than the above-described detailed description, and all changes or modifications derived from the meaning and scope of the claims and their equivalents should be interpreted as being included in the scope of the present invention.

The invention claimed is:

1. A multiple molecular diagnosis chip structure, comprising:
   a reaction pad having a sample passage hole formed therethrough and a plurality of reaction patterns formed thereon, wherein an injected sample to be diagnosed can pass through the sample passage hole, and wherein a reaction solution that includes an isothermal amplification primer for a specific nucleic acid of a subject to be diagnosed, an amplification enzyme, and an indicator having varying fluorescence depending on whether amplification occurs, is comprised in the reaction patterns;
   a channel pad disposed on the lower surface of the reaction pad, the channel pad having a first sample passage channel formed in a position corresponding to the sample passage hole, and a plurality of second sample passage channels corresponding to the reaction patterns; and
   a transfer pad disposed on the lower surface of the channel pad to transfer a sample, which is injected from the sample passage hole and transferred through the first sample passage channel, to the reaction patterns through the plurality of the second sample passage channels.

2. The multiple molecular diagnosis chip structure of claim 1, wherein the reaction solution further comprises polyvinyl alcohol (PVA).

3. The multiple molecular diagnosis chip structure of claim 1, further comprising a cover disposed on an upper surface of the reaction pad and having a sample injection port formed in a position corresponding to the sample passage hole.

4. The multiple molecular diagnosis chip structure of claim 1, wherein the reaction pattern is formed of a comparison pattern capable of confirming whether a sample is input and at least two detection patterns capable of detecting a specific DNA contained in a sample to be diagnosed,
   wherein the isothermal amplification primer and an amplification enzyme with regard to each separate specific DNA exist in the detection patterns.

5. The multiple molecular diagnosis chip structure of claim 1, further comprising: an upper case which is formed at an upper portion of the reaction pad and formed with a sample input part corresponding to the sample passage hole and a pattern confirmation part formed in a position corresponding to the reaction pattern, and a lower case which is formed at a lower portion of the transfer pad and is coupled with the upper case.

6. The multiple molecular diagnosis chip structure of claim 1, wherein the reaction pad is a porous glass membrane.

7. The multiple molecular diagnosis chip structure of claim 1, wherein the channel pad is a nitrocellulose or polyether sulfone membrane.

8. The multiple molecular diagnosis chip structure of claim 1, wherein the transfer pad is a membrane having an asymmetric structure in which a pore size is reduced in a downward direction.

9. The multiple molecular diagnosis chip structure of claim 1, wherein the indicator comprises HNB (Hydroxynaphthol Blue).

\* \* \* \* \*